United States Patent
Takahashi et al.

(10) Patent No.: US 7,504,627 B2
(45) Date of Patent: *Mar. 17, 2009

(54) ELECTRON BEAM INSPECTION APPARATUS

(75) Inventors: Masakazu Takahashi, Tsuchiura (JP); Satoru Yamaguchi, Hitachinaka (JP); Masashi Sakamoto, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/878,361

(22) Filed: Jul. 24, 2007

(65) Prior Publication Data

US 2007/0272860 A1    Nov. 29, 2007

Related U.S. Application Data

(63) Continuation of application No. 11/099,688, filed on Apr. 6, 2005, now Pat. No. 7,256,400.

(30) Foreign Application Priority Data

Apr. 9, 2004    (JP) .............................. 2004-114859

(51) Int. Cl.
  *H01J 37/28*    (2006.01)
  *G01N 23/225*    (2006.01)
(52) U.S. Cl. ....................... 250/310; 250/307
(58) Field of Classification Search ....................... None
See application file for complete search history.

(56) References Cited

U.S. PATENT DOCUMENTS

| 5,200,677 | A | 4/1993 | Dueck et al. |
| 6,576,919 | B1 | 6/2003 | Yoshida |
| 6,583,414 | B2 | 6/2003 | Nozoe et al. |
| 6,657,221 | B2 | 12/2003 | Nakagaki et al. |
| 7,076,761 | B2 | 7/2006 | Inanami et al. |
| 7,256,400 | B2 * | 8/2007 | Takahashi et al. ........... 250/310 |

FOREIGN PATENT DOCUMENTS

| JP | 02-159683 | 6/1990 |
| JP | 09-283582 | 10/1997 |
| JP | 11-40631 | 2/1999 |
| JP | 2004-079792 | 3/2004 |

* cited by examiner

*Primary Examiner*—Jack I Berman
(74) *Attorney, Agent, or Firm*—McDermott Will & Emery LLP

(57) ABSTRACT

An electron beam inspection apparatus in which the order of inspection is determined to shorten the inspection time is disclosed. The order of inspection is determined by minimizing the total of the moving time and the inspection time as well as by simply optimizing the covered distance. At the time of preparing a recipe to determine the inspection points and the order of inspection, the sequence of a series of inspection points sequentially inspected is changed to optimize the order of inspection. Not only the sequence which minimizes the covered distance is determined but also the order of inspection of the inspection points is optimized in accordance with the charged state, warping of the wafer, the delivery position and other situations.

10 Claims, 14 Drawing Sheets

AVERAGE COVERED DISTANCE : 3.66 CHIPS

AVERAGE COVERED DISTANCE : 2.31 CHIPS

AVERAGE COVERED DISTANCE : 2.87 CHIPS

FIG. 11A
FIG. 11B
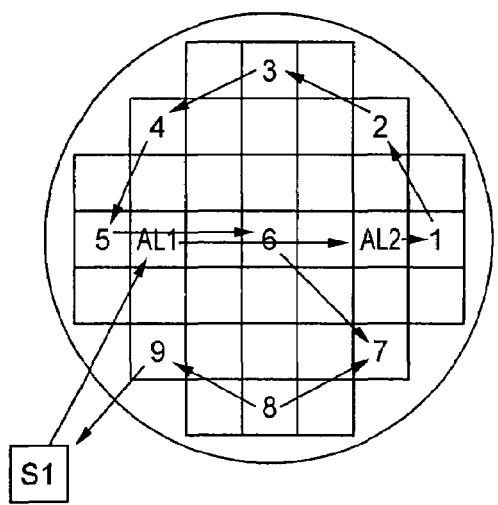
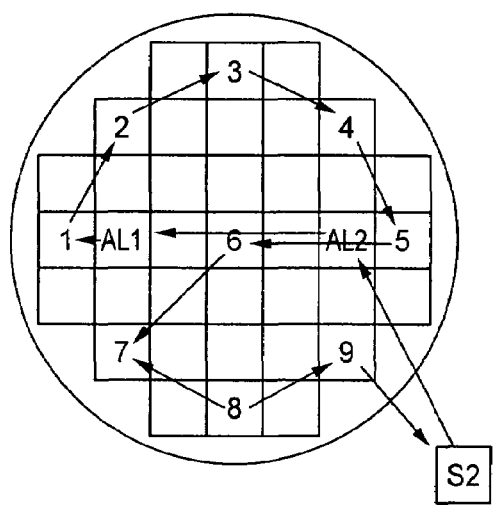

EQUIPOTENTIAL LINES

OPTIMUM ROUTE BY COVERED DISTANCE WITH 8 TOTAL POTENTIAL VARIATIONS

EQUIPOTENTIAL LINES

OPTIMUM ROUTE ALONG EQUIPOTENTIAL LINE WITH 2 TOTAL POTENTIAL VARIATIONS ns type).
ELECTRON BEAM INSPECTION APPARATUS This application is a Continuation of U.S. application No. 11/099,688, filed Apr. 6, 2005, now U.S. Pat. No. 7,256,400, claiming priority of Japanese Application No. 2004-114859, filed Apr. 9, 2004, the entire contents of each of which are hereby incorporated by reference.

BACKGROUND OF THE INVENTION

This invention relates to an electron beam inspection apparatus in which a plurality of inspection points are moved to shorten the inspection time.

The inspection points are arranged by the user arbitrarily and hence in an inefficient order of inspection. To assure efficiency, a method is also available to arrange the inspection points in the form of bellows. In this arrangement in bellows form, however, the inspection time is not necessarily minimized. The inspection time is increased conspicuously due to the increased distance in the inspection of a wafer having a diameter as large as 300 mm. Therefore, the optimization of the order of inspection is required and has not been realized due to the failure to establish an algorithm which completes the calculation in practical calculation time.

SUMMARY OF THE INVENTION

The object of this invention is to provide an electron beam inspection apparatus in which the calculation function for determining the order of inspection is realized to shorten the inspection time. The calculation should desirably be completed in a practicable range of not longer than 30 seconds. The order of inspection is determined by shortening the total time including the moving time and the inspection time as well as the distance covered.

According to this invention, there is provided an electron beam inspection apparatus wherein the function to optimize the order of inspection is realized at the time of preparing a recipe to determine the inspection points and the order of inspection. The inspection apparatus has the function not only to determine the order of inspection for shortening the distance covered but also to optimize the order of inspection of inspection points in accordance with the carrying-out position and other prevailing situations. After determining the inspection points, the order of inspection is changed using the order changing function. The formula used to change the order of inspection is automatically selected in accordance with the number of inspection points involved.

As described above, the inspection time is shortened by changing the order of inspection of the inspection points in an electron beam inspection apparatus thereby to contribute to an improved throughput.

Other objects, features and advantages of the invention will become apparent from the following description of the embodiments of the invention taken in conjunction with the accompanying drawings.

BRIEF DESCRIPTION OF THE DRAWINGS

FIGS. 11A and 11B show an example in which an optimum route is acquired for each of two wafer carrying-out positions taking the alignment point into consideration.

DESCRIPTION OF THE INVENTION

Figure 1:
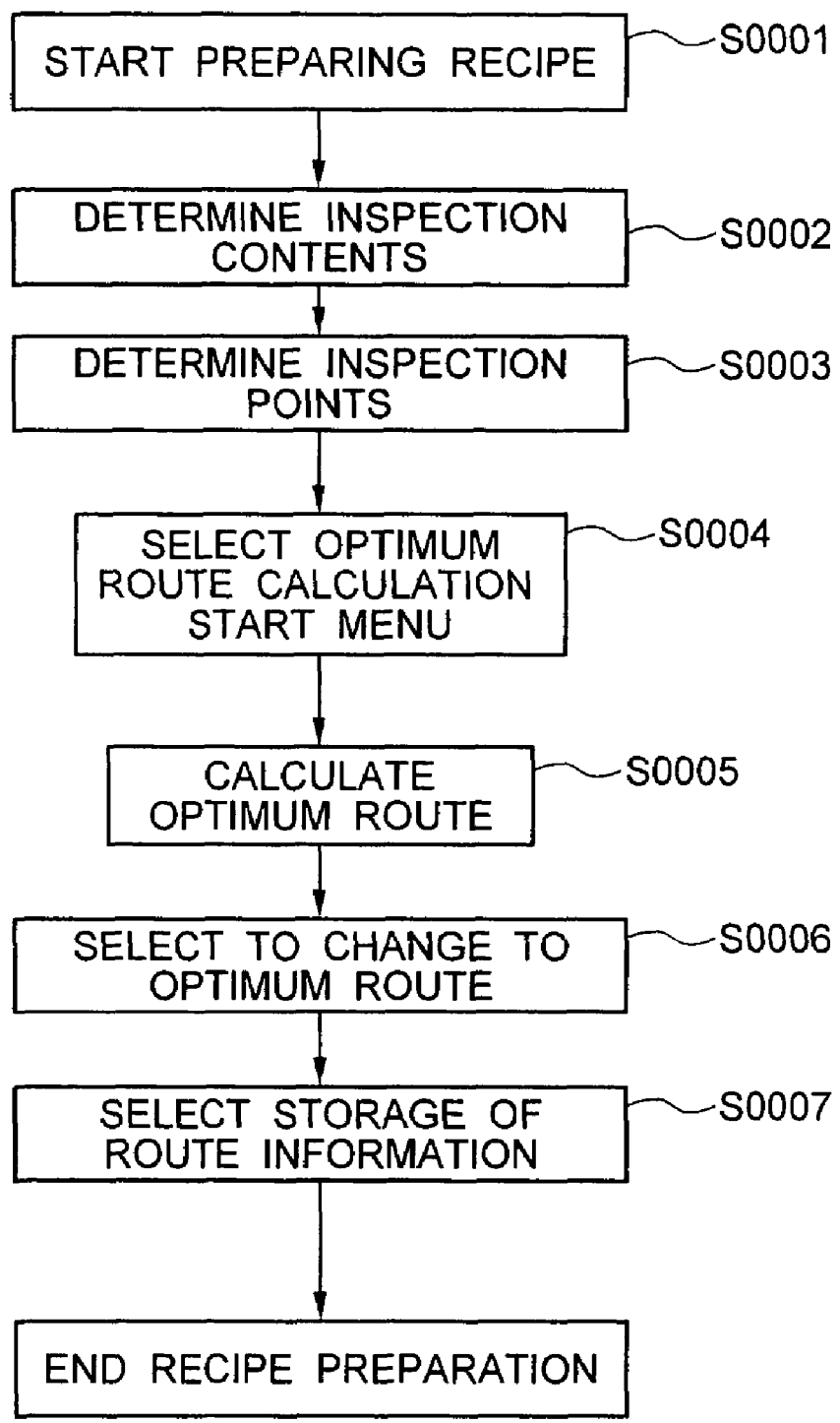
FIG. 1 shows the process for preparing a recipe.

A basic operation flow of the invention is shown in FIG. 1. In the conventional recipe preparation process, the inspection points are determined arbitrarily by the user, and the apparatus performs the inspection in accordance with the procedure thus determined. According to this invention, the recipe begins to be prepared (S0001), the contents of inspection are determined (S0002) and the inspection points are determined (S0003), after which an optimum route calculation menu (102) is selected (S0004) from an optimum route calculation and select screen (100) shown in FIG. 16. Upon selection (S0004) of the optimum route calculation menu (102), the calculation of the optimum route is started (S0005). The optimum route is calculated automatically. After calculation of the optimum route, the order of inspection of the optimum route is indicated on an inspection point list (101). The change in the order of inspection is selected (S0006), and an OK button (106) is selected (S0007) on the route information storage confirmation screen (105) thereby to determine the optimum route. No route information is stored in the case where the "cancel" button (107) is selected. Steps S0004 to S0007 represent new steps added by the invention. The selection of the optimum route calculation start menu, the route information storage confirmation, etc. are conducted by use of an input device (52) while watching a CRT (53) shown in FIG. 15. The route information, together with the recipe information, are stored in a storage unit (51).

Figure 2:
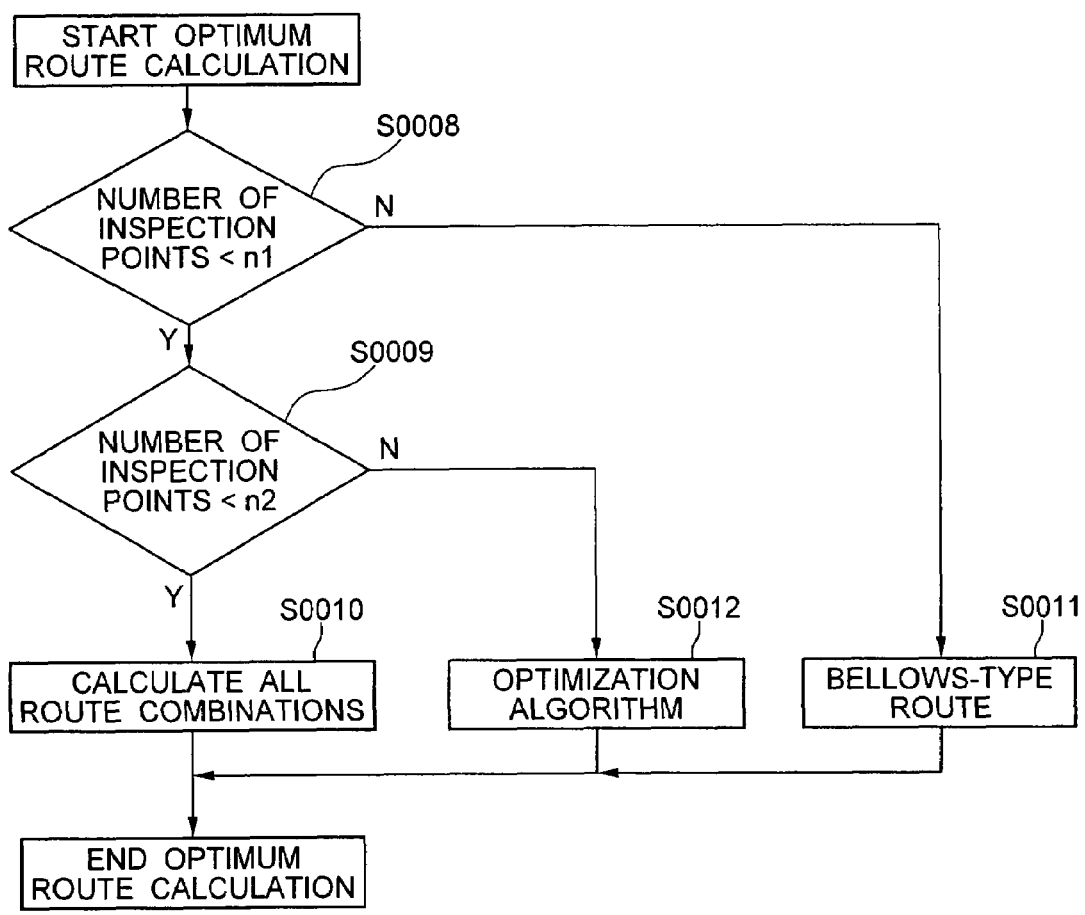
FIG. 2 shows an outline of the process for calculating an optimum route.

The calculation process of the optimum route is shown in FIG. 2. Strictly, the optimum route cannot be determined without calculating all the combinations of the inspection orders. With the increase in the inspection points, however, the number of combinations increases and all the combinations cannot be calculated within a practical calculation time. According to this invention, the calculation algorithm is changed in accordance with a predetermined number of measurement points. In the case where the number of measurement points is smaller than n1 and n2, all the route combinations are calculated to calculate the optimum route strictly (S0008, S0009, S0010). In the case where the measurement points exceed n1 and n2, on the other hand, an optimum route is calculated approximately by the optimization calculation algorithm or the bellows-type route calculation (S0011, S0012).

Figure 3:
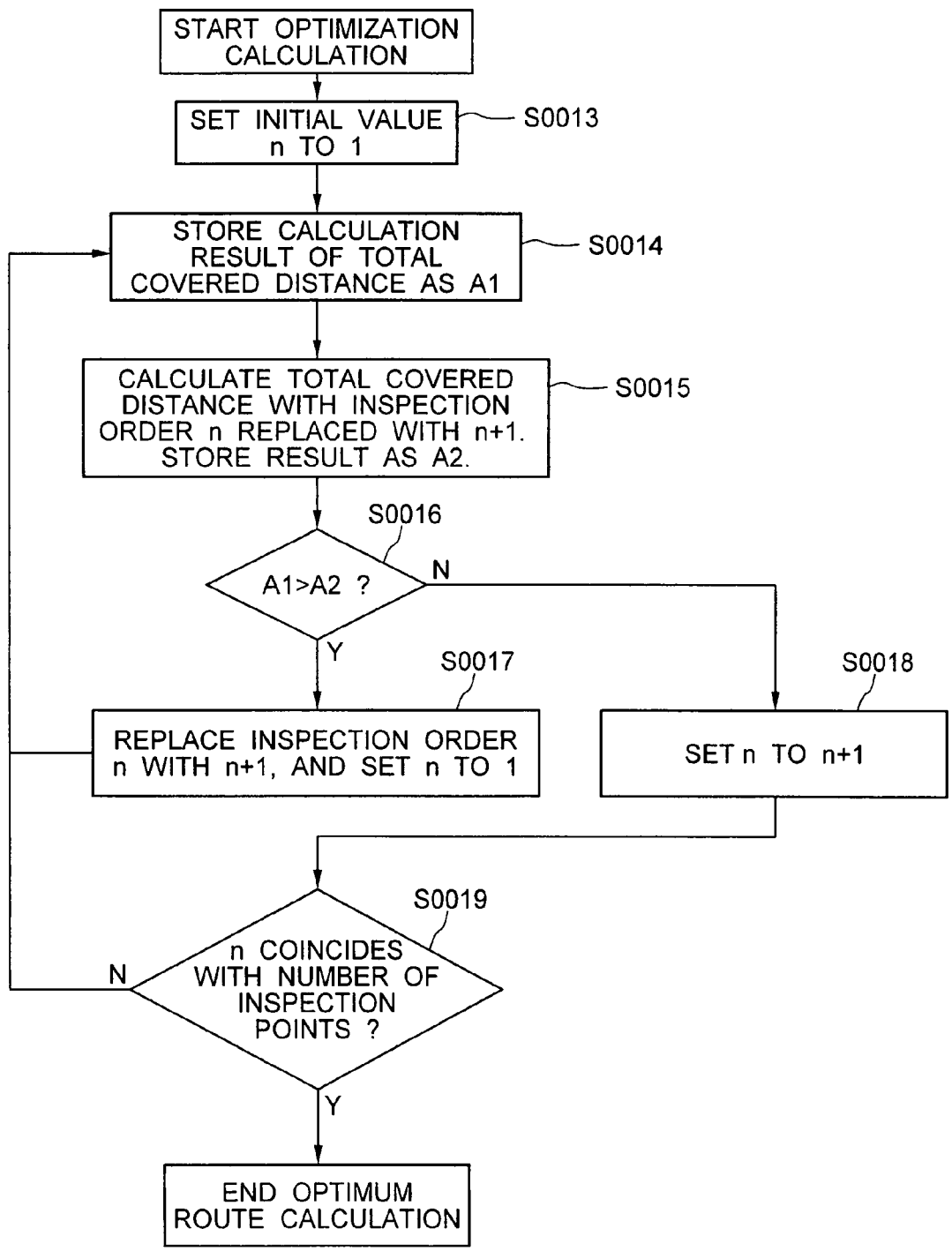
FIG. 3 shows the process of calculation to determine an optimum route.

An example of the algorithm to calculate an optimum route is shown in FIG. 3. According to this algorithm, continuous inspection points in a predetermined order of inspection are changed and the inspection time is compared. Then, the order of inspection which shortens the inspection time is selected. First, an initial value n is set to 1 (S0013). Then, the calculation result of the total covered distance is stored as A1 (S0014). The inspection order n is replaced with the inspection order n+1 and the total covered distance is calculated, the result of which is stored as A2 (S0015). In the case where A1 is larger than A2, the inspection order n is replaced with n+1 so that n is set to 1 and the process is returned to S0014 (S0016, S0017). In this case, n is set to 1 at S0017 and the process is returned to S0014. Nevertheless, n may be alternatively set to n−1 at S0017. In the case where A2 is larger than A1, on the other hand, n is set to n+1, and in the case where n coincides with the number of inspection points, the inspection is completed. Otherwise, the process is returned to S0014 (S0018, S0019).

The route after calculation follows exactly the same order as before calculation or the order with a shorter inspection time than before calculation. The calculation time is also comparatively shortened. Since only the continuous inspection points are replaced for comparison, however, the route after calculation considerably depends on the route before calculation. Depending on the manner in which the route before calculation is selected, therefore, the optimum route may fail to be determined. For this reason, this algorithm is more effectively used only after determining an approximately optimum route by another algorithm to determine the optimum route.

Figure 4:
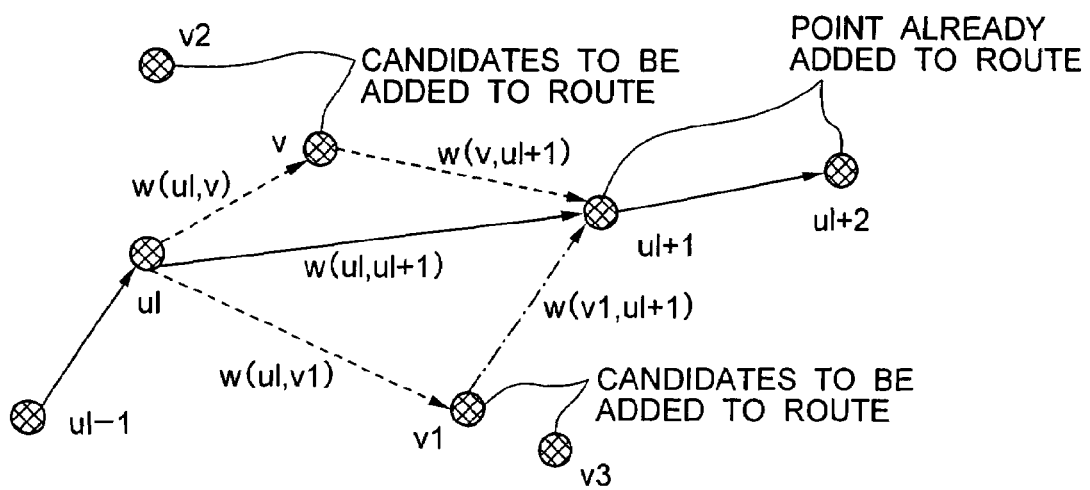
FIG. 4 shows the process of calculation to determine an optimum route.

Next, another example of the algorithm to calculate the optimum route is shown in FIG. 4. In this calculation method, the starting and ending points are defined first of all, and using them as an inspection route, inspection points are added (inserted) in the inspection route. The candidate points to be added (inserted) are those not yet added to the route, and inspection points minimizing the inspection time for the whole route are inserted in the order minimizing the inspection time. In FIG. 4, points u1−1, u1, u1+1, u1+2 are already added to the inspection route, and points v, v1, v2, v3 candidates to be added to the route. Specifically, the following procedure is followed.

Assume that the input is a weighted complete graph G at the position p with the side weight satisfying the triangle inequality $w(u, v)+w(u, w) \geq w(v, w)$ at arbitrary three input points u, v, w. The output is assumed to be a Hamilton closed path C of appropriate weight.

1. Select uEV (G), and regard u as 1 minus closed path C1. (i←1)
2. If i=p, end as C=Cp.
3. If i . p, select a point v where $w(u1, v)+w(v, u1+1)-w(u1, u1+1)$ is minimum out of points adjacent to continuous points u1, u1+1 on Ci but not on C.
4. By setting i←i+1, repeat the processes 2 to 4 above.

As a result, in the case of FIG. 4, $w(u1, v)+w(v, u1+1)<w(u1, v1)+w(v1, u1+1)$, and therefore v is inserted in the route.

This calculation is repeated until all the inspection points are added to the route. This method, as compared with the method of FIG. 3, has the feature that the calculation time increases with the number of inspection points. Since this method is hardly affected by the initial route, however, a route comparatively near to the optimum route can be calculated. An effective method is to use this algorithm and then the algorithm of FIG. 3.

This invention is not limited to the aforementioned algorithms, but can use, for example, TSP (traveling salesman problem) or the nearest inspection algorithm in public domain as a method of calculating the optimum route.

Figure 5:
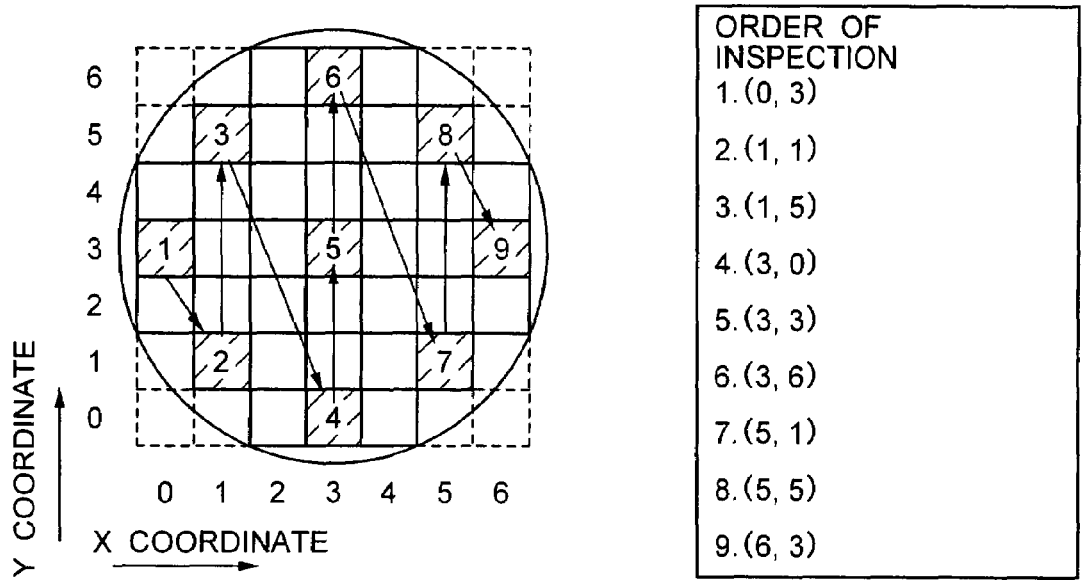
FIG. 5 shows the normal order of inspection.
Figure 6:
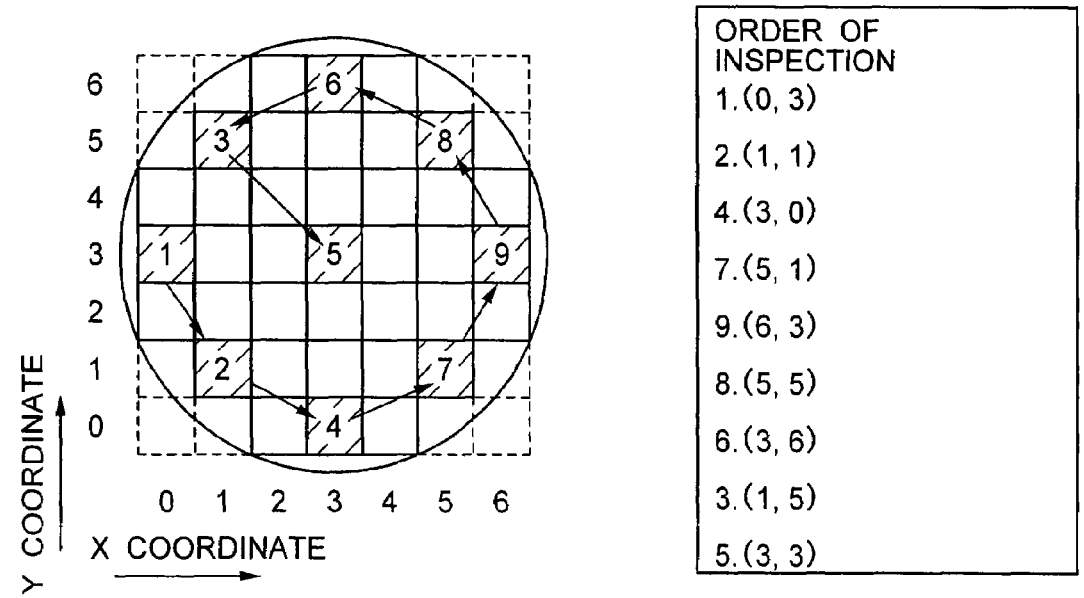
FIG. 6 shows the order of inspection in the shortest distance.
Figure 7:
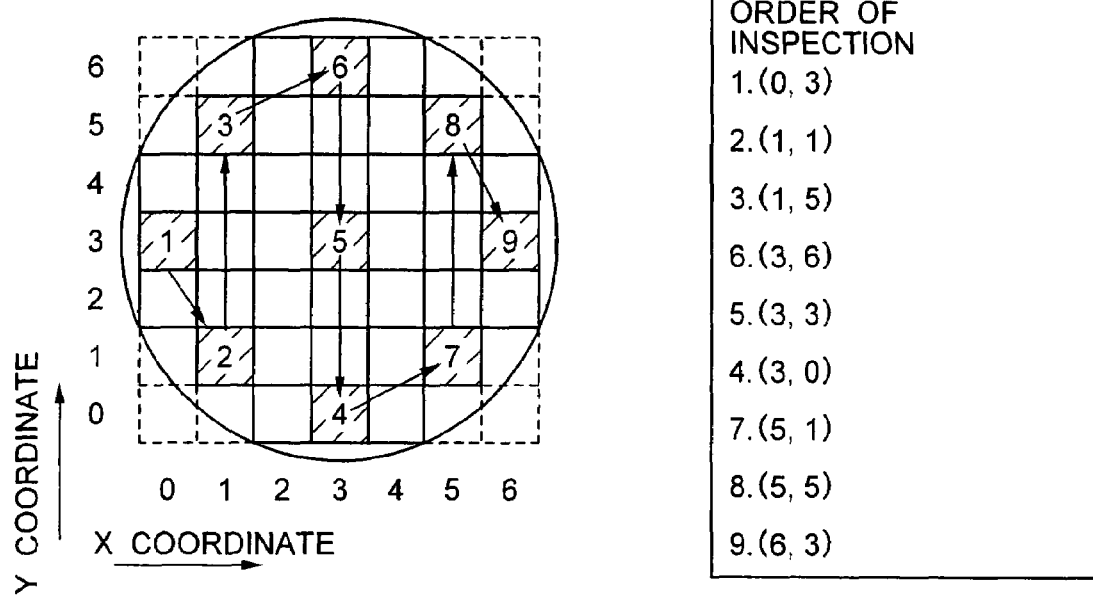
FIG. 7 shows the order of inspection in bellows type (return type).

The result of calculation of the optimum route is explained with reference to the examples shown in FIGS. 5 to 7. FIG. 5 shows a case in which the inspection is conducted in the ascending order of both X and Y coordinates. This order of inspection is often determined arbitrarily by the user. In this inspection order, the total distance between inspection points is not shortest, and therefore the total inspection time can be reduced by changing the order of inspection. FIG. 6 shows the result of determining the optimum route using the functions of the invention. The optimum route is not necessarily determined uniquely, and this route is an example of the optimum route. The average covered distance is 3.66 chips for the route shown in FIG. 5, while the figure for the optimum route is 2.31 chips or about 40% shorter. This example assumes that the covered distance is proportional to the inspection time. In actual calculations, however, parameters other than the covered distance can be used, as described in detail later. FIG. 7 shows an example of a bellows-type route. The inspection is conducted in the ascending order of X coordinate as in FIG. 5, while the ascending order and the descending order are alternated with each other in Y direction. As a result, the number of reciprocations in Y direction can be reduced. Thus, the total covered distance and hence the total measurement time can be reduced. The average covered distance along the route shown in FIG. 7 is 2.87 chips. In this case, as compared with FIGS. 5 and 7, the average covered distance is reduced by about 20%.

Figure 8:
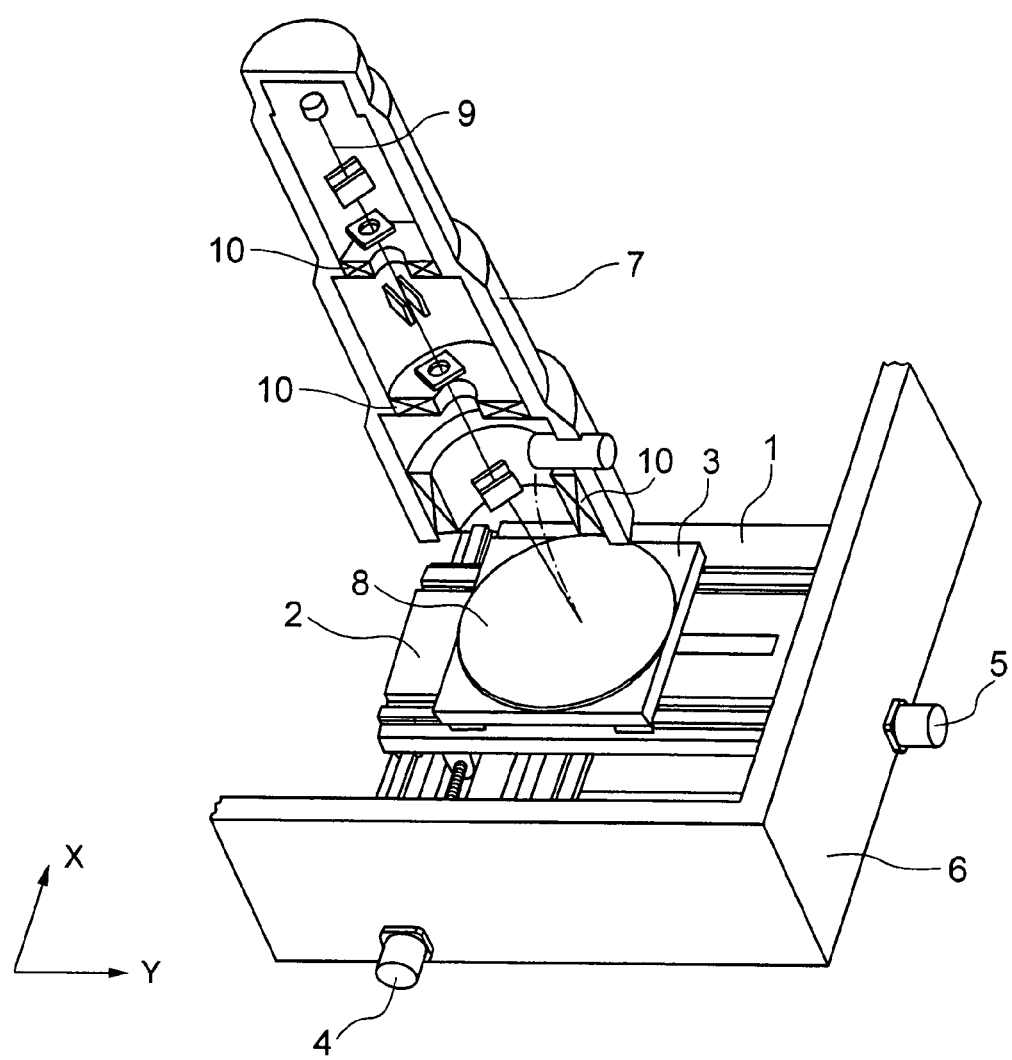
FIG. 8 shows an outline of a measuring SEM.

This invention is effectively applicable to the measuring SEM and the review SEM in which as shown in FIG. 8, the inspection is conducted on a sample 8 moved by moving an X table 2 and a Y table 3 controllable while at the same time radiating an electron beam 9. Also, apart from the inspection apparatus using an electron beam, the invention is effectively applicable to a case in which the inspection range is narrow and the inspection points are moved while moving the sample 8. Although the XY stages are used to move the sample 8 in the case under consideration, the invention is also applicable to a Rθ stage having a rotary shaft and an axis to move the stage or a case in which the stage moves along one axis and the electron beam along an axis perpendicular thereto. Further, in FIG. 8, 1 denotes a base, 4 denotes an X-axis motor, 5 denotes a Y-axis motor, 6 denotes a sample chamber, and 7 denotes a main body.

Figure 9:
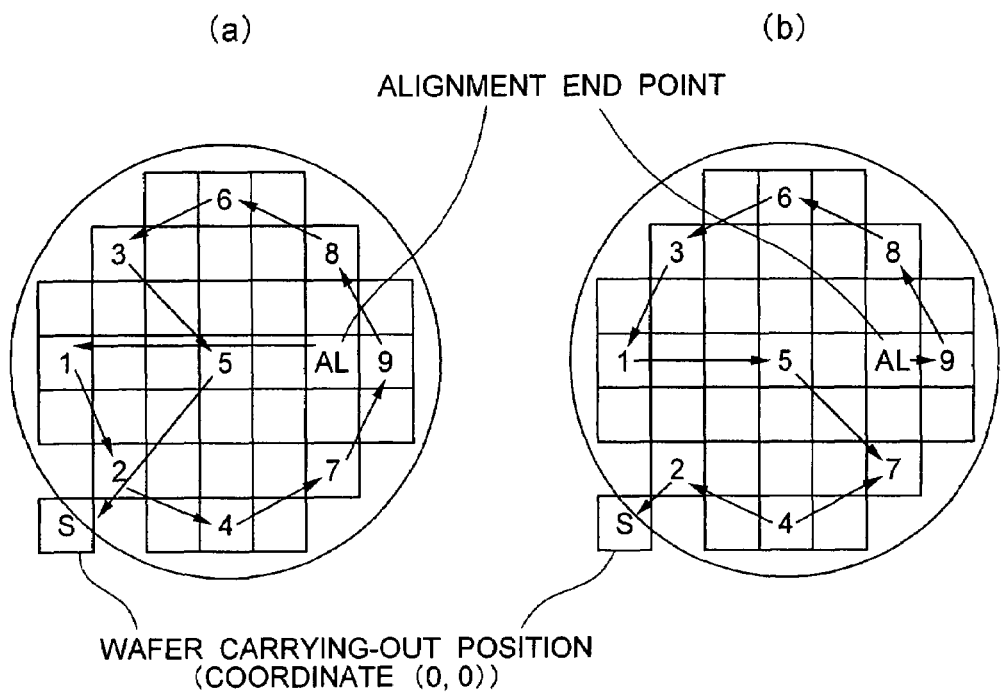
FIG. 9 shows a route determined taking the alignment end point and the wafer carrying-out position into consideration.

FIGS. 9 to 11B show an application of the invention to the measuring SEM. In the measuring SEM, before moving the inspection points to conduct the inspection, an image is recognized at a predetermined alignment point to adjust the wafer coordinate. The moving time from the alignment point before moving to the inspection points, therefore, is also a factor contributing an increased total measurement time. Also, after the last inspection session, the sample 8 is moved to a wafer carrying-out position before moving to a preliminary exhaust chamber. In optimization of the total moving time, therefore, the moving time from the last inspection point to the wafer carrying-out position is also preferably included in the calculation. FIG. 9 shows a case in which the movement from the alignment end point to the inspection point and the movement from the last inspection point to the wafer carrying-out position are also included in the calculation. In the optimum route of FIG. 9(a) in which only the inspection points are considered in the calculation, the average covered distance is 2.77 chips, while the average covered distance is 2.17 chips or about 20% smaller for the route shown-in FIG. 9(b) in which the movement from the alignment end point to the inspection points and the movement from the last inspection point to the wafer carrying-out position are included in the calculation.

Figure 10:
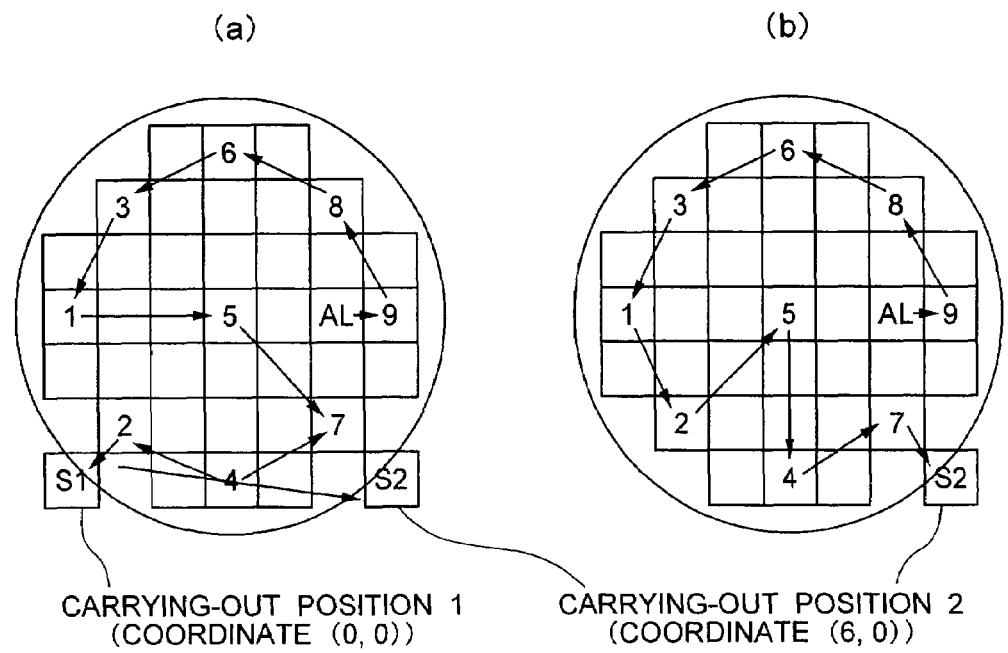
FIG. 10 shows an optimum route for each of two wafer carrying-out positions.

FIG. 10 shows an application to a plurality of preliminary exhaust chambers. In this apparatus, the optimum route for the carrying-out position 1 is not necessarily the optimum route for the carrying-out position 2. In the route shown in FIG. 10(a), the average covered distance is 2.17 chips for carrying out to the carrying-out position 1, and 2.68 chips for carrying out to the carrying-out position 2. In the case where the route shown in FIG. 10(b) is followed, however, the covered distance is 2.17 chips for the carrying-out position 2. In this way, a plurality of optimum routes are prepared using the algorithm of the invention, and in accordance with the wafer carrying-out position for inspection, an appropriate one of the optimum routes is selected. Thus, the optimum route can be inspected in keeping with the conditions.

The example shown in FIGS. 11A and 11B represents a case in which the sequence of a plurality of alignment points is also taken into account for optimization. A plurality of alignment points are generally used. In the measurement sequence from the wafer carrying-in position (normally the same as the carrying-out position) through all the alignment points and all the inspection points to the carrying-out position, therefore, the route shortest in inspection time is calculated as an optimum route.

Figure 12A:
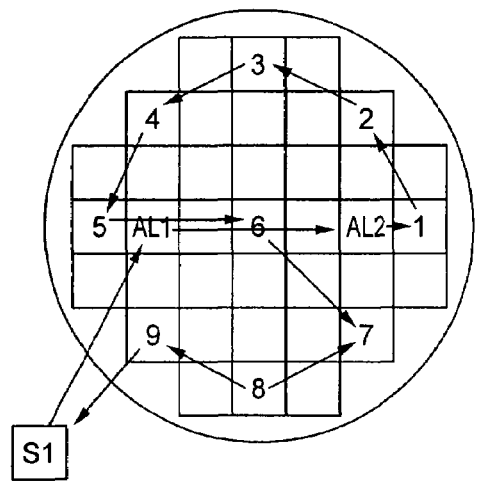
FIGS. 12A, 12B and 12C show an example using an optical microscope for alignment.
Figure 12B:
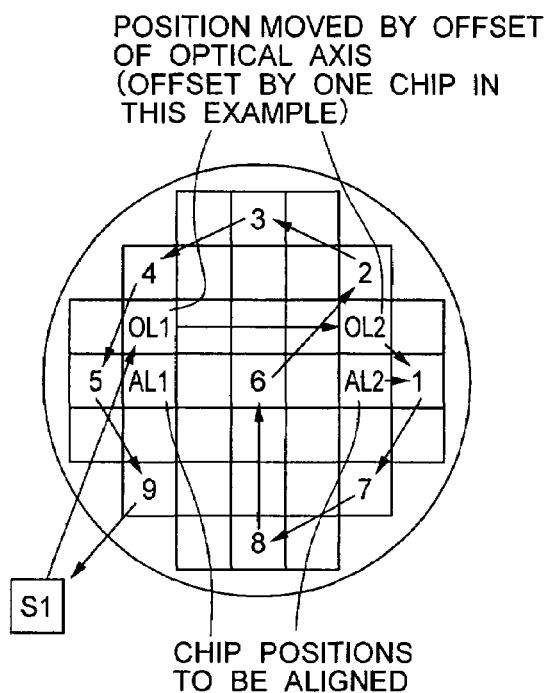
Figure 12C:
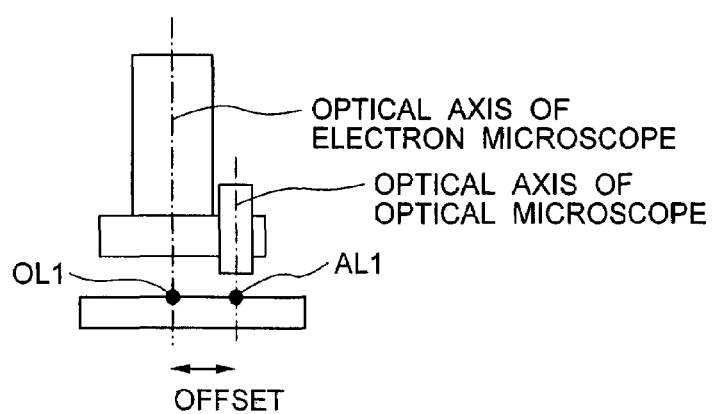

In the case where alignment is carried out using an optical microscope, the calculation is further required taking the offset into consideration. As shown in FIG. 12C, the optical axes of the optical microscope and the electron microscope are offset from each other, and in the case where a point AL1 is inspected under the optical microscope, the point AL1 is moved to the axial position of the optical microscope. Under this condition, a chip OL1 is located at the position on the optical axis of the electron microscope. This chip is moved to OL1 in terms of the coordinate system observed under the electron microscope. In the coordinate of the alignment points for calculating the optimization, therefore, the offset is required to be automatically calculated while the moving position is regarded as OL1 for calculation. The offset amount is unique to each apparatus, and defined in advance. Therefore, this distance can be used for conversion. In the case where the alignment is conducted using the same chip AL1 under electron microscope, on the other hand, as shown in FIG. 12A, conversion from the chip AL1 is required, while the alignment using the optical microscope requires the conversion to the position of OL1 as shown in FIG. 12B before optimization calculation. In this way, the optimum route is calculated in FIG. 12B.

Figure 13A:
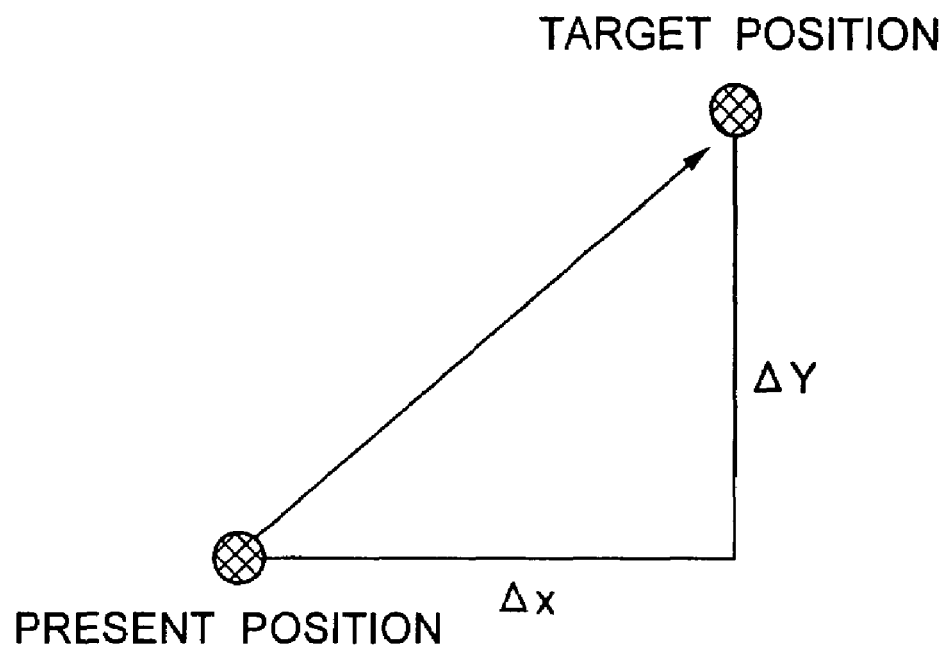
FIGS. 13A and 13B show the calculation of the moving time to determine the optimum route.
Figure 13B:
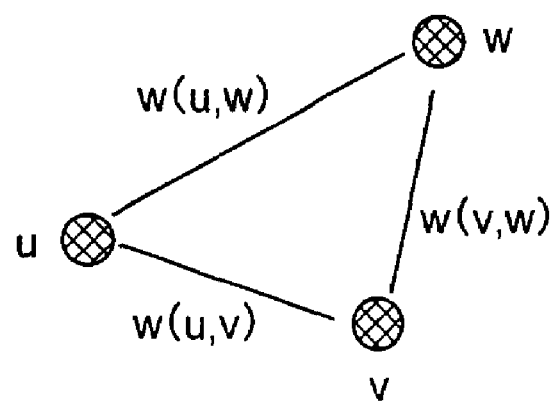

The foregoing explanation concerns a case in which the total inspection time is minimized by minimizing the total covered distance. In this case, the moving time T is proportional to $\sqrt{((\Delta X)^2+(\Delta Y)^2)}$ in FIG. 13A. In the stage adapted to move in X and Y directions independently of each other, the total moving time is that along X or Y direction, whichever is longer. On such an XY stage, therefore, the moving time in X direction and the moving time in Y direction are calculated from the coordinates before and after movement, so that the moving time is determined from the longer one of the distances. In such a case, the moving time T is proportional to MAX($\Delta X$, $\Delta Y$). Generally, in FIG. 13B, assume a weighted complete graph G at the input position p with the side weight satisfying the triangle inequality $w(u, v)+w(u, w) \geq w(v, w)$ at arbitrary three input points u, v, w. Then, the optimum route can be calculated using the optimization algorithm. The moving time, etc. which satisfy the equation above, can be used for calculation.

Figure 14A:
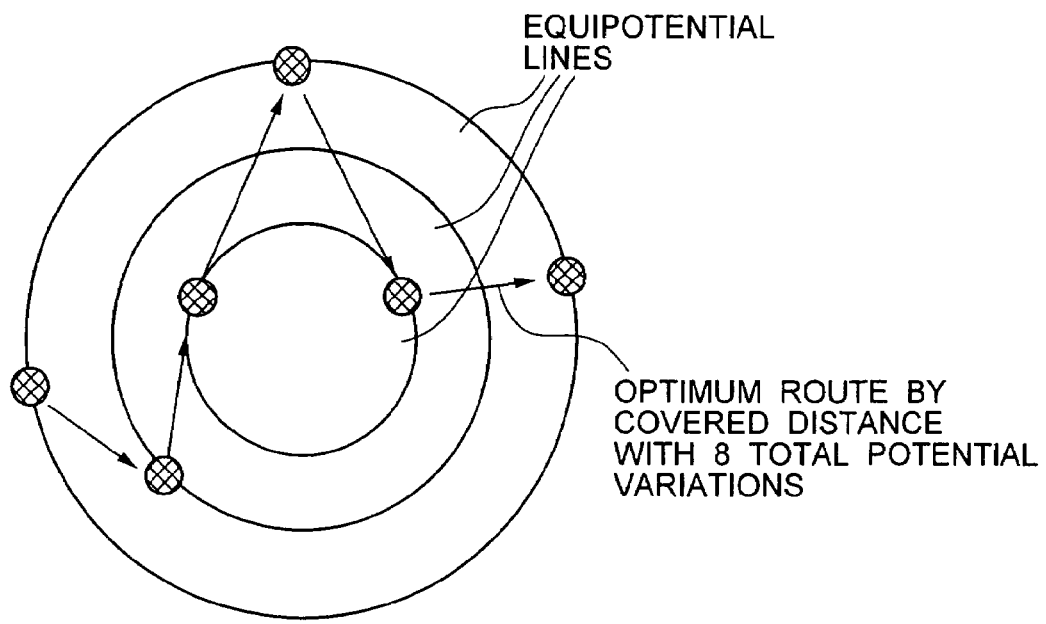
FIGS. 14A and 14B show an example in which the time other than the moving time can be shortened by the route.
Figure 14B:
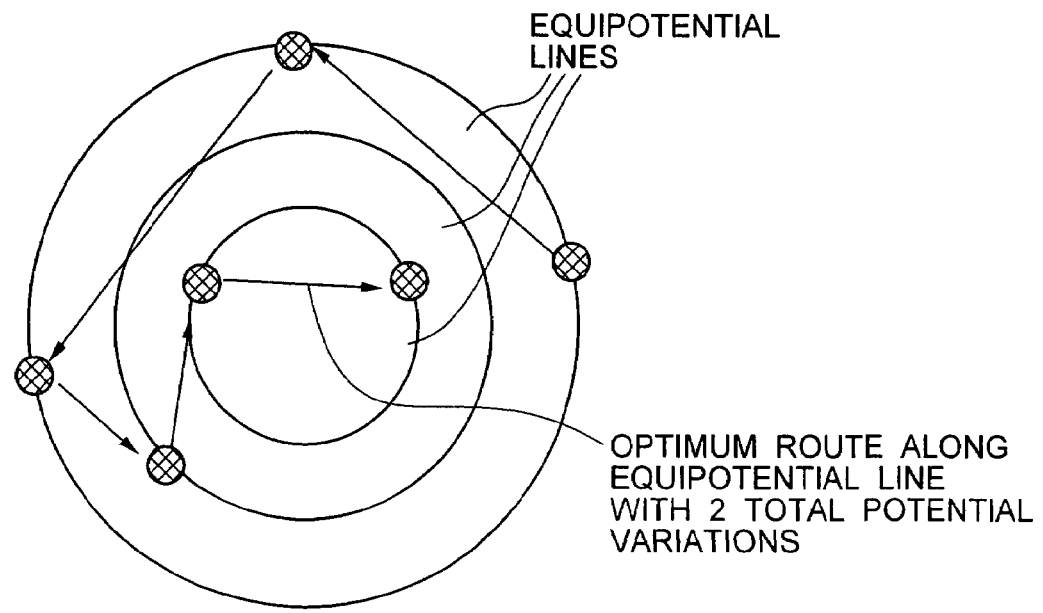

FIG. 14 shows a case in which the parameters other than the covered distance are controlling over the measurement time. In the case where the sample surface is known to be charged like a contour and the time required for correction is longer than the moving time of the sample, for example, the total inspection time can be minimized by conducting the inspection in such an order as to minimize the correction amount. The optimum route in terms of the covered distance shown in FIG. 14A is accompanied by a total of eight potential variations, while the optimum route along the equipotential line shown in FIG. 14B has a total of two potential variations. Also in this case, the optimum route can be calculated following the procedure according to the invention by expressing the correction time due to the potential difference between the inspection points in numerical values.

Figure 18:
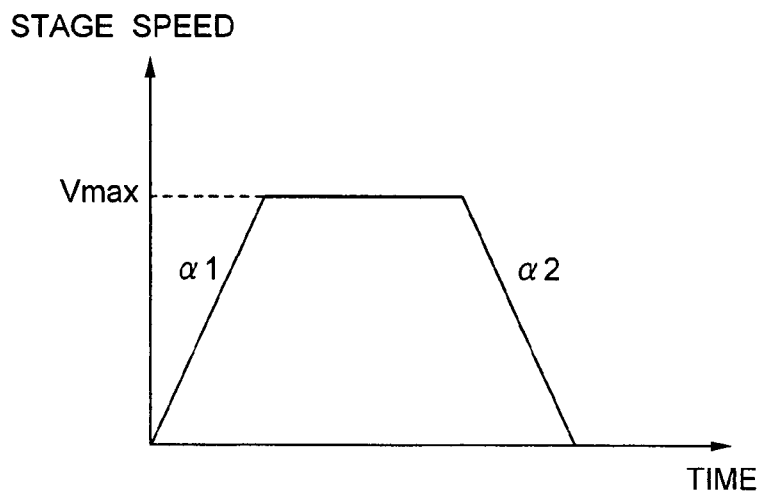
FIG. 18 shows an example of the trapezoidal control operation of the stage speed.

The process of minimizing the total inspection time with the wafer height change $\Delta h$ as a parameter is explained with reference to FIGS. 15 and 18. Generally, the height of each inspection point on a wafer 20 is varied by a least 100 μm even on the stage 25, and since the focal depth of the SEM is less than 1 μm, the focusing is impossible. In view of this, a height detecting laser 26 is applied to the wafer 20, and the reflection thereof is detected by a laser detector 27 to measure the height. Based on the height information obtained by the measurement, the current for an objective lens 17 is controlled by an objective lens control power supply 33 through a computer 50 to attain the focusing. The objective lens 17 reacts to the set current with a predetermined time constant (delay). Specifically, the larger the change of the current, the longer the time required to set a target focal point. Further, while the objective lens current is directly changed, the image is picked up and the sharpness is determined. Thus, the automatic focusing operation (AF) is conducted by setting an objective lens current associated with the highest sharpness.

Figure 15:
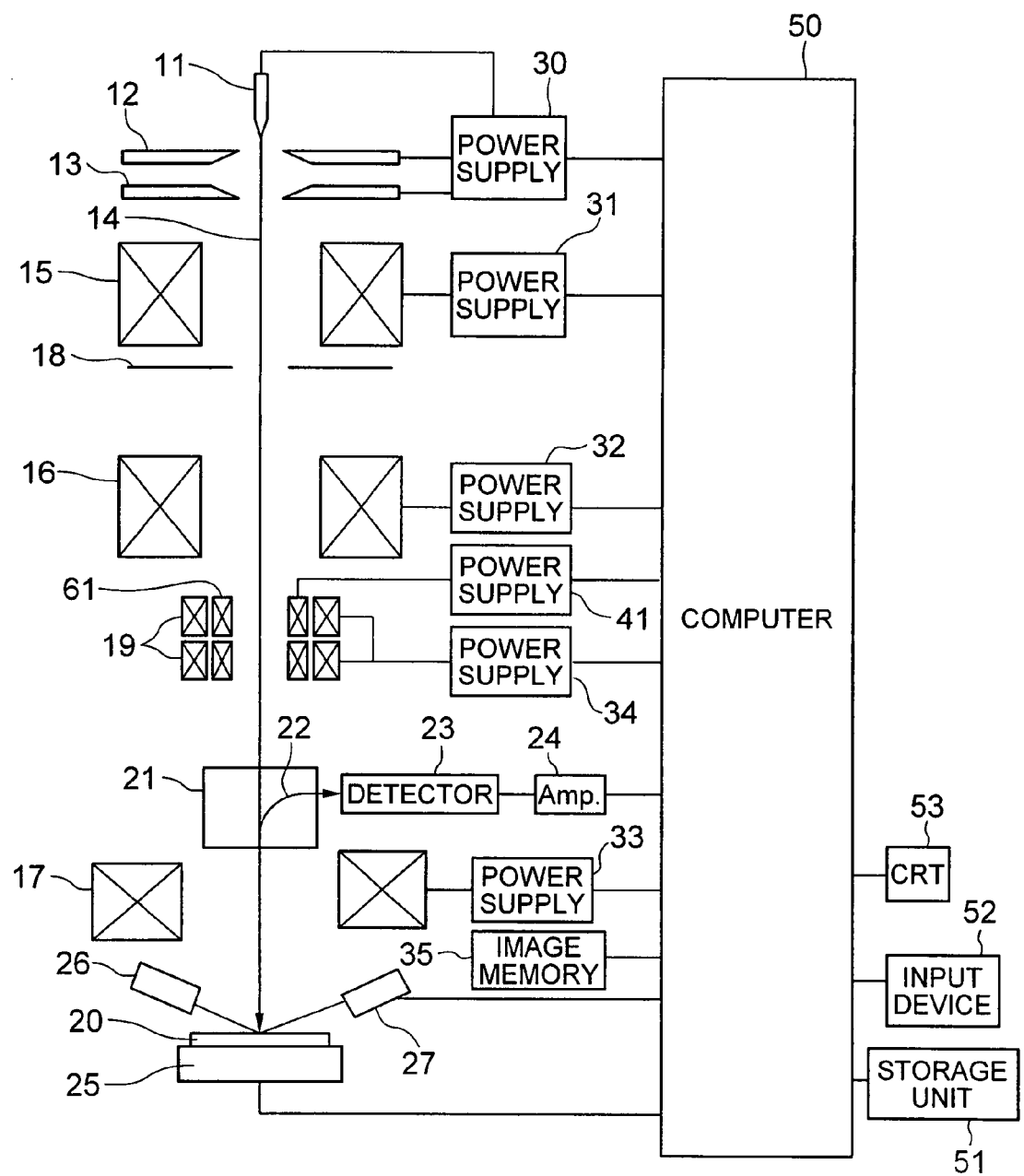
FIG. 15 is a diagram showing a general configuration of a scanning electron microscope according to an example of the invention.
Figure 16:
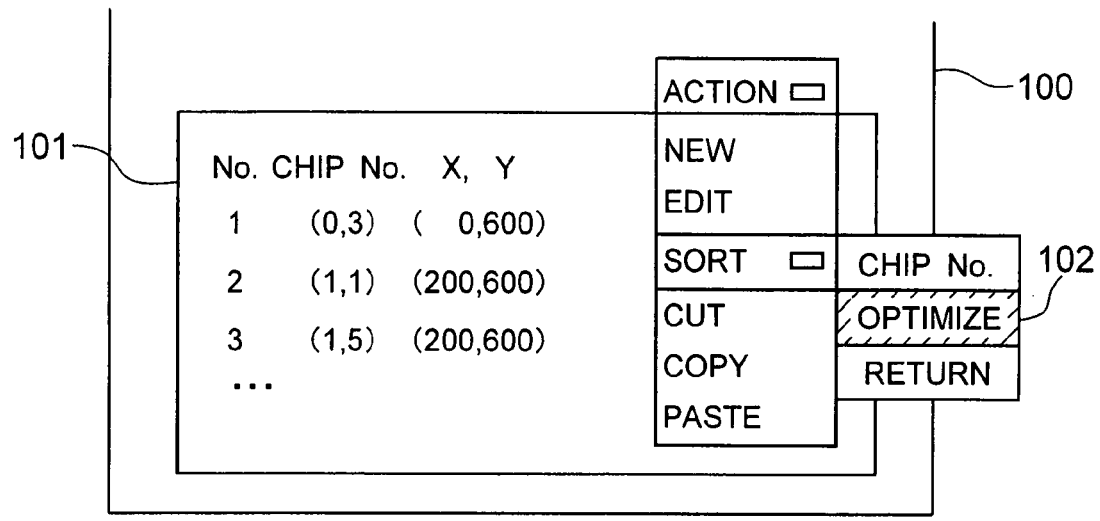
FIG. 16 shows the selection by calculation of an optimum route.
Figure 17:
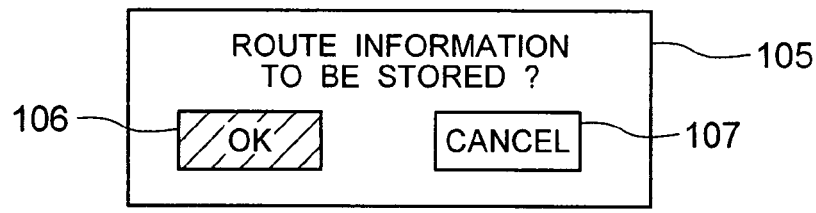
FIG. 17 shows a screen to store the route information.

Further, in FIG. 15, 11 denotes a cathode, 12 denotes a first anode, 13 denotes a second anode, 14 denotes an electron beam, 15 denotes a first convergence lens, 16 denotes a second convergence lens, 18 denotes an aperture plate, 19 denotes a scanning coil, 21 denotes an orthogonal electromagnetic field (E×B) for separating secondary signals, 22 denotes the secondary signals, 23 denotes a detector for secondary signals, 24 denotes an amplifier, 30 denotes a power supply for controlling a high voltage, 31 denotes a power supply for controlling the first convergence lens, 32 denotes a power supply for controlling the second convergence lens, 34 denotes power supply for controlling the scanning coil, 35 denotes an image memory, 41 denotes a power supply for controlling an aligner for the objective lens, and 61 denotes an aligner for the objective lens.

In executing the recipe, let Ts be the stage moving time to move the stage to an inspection point, and T1 the reaction waiting time due to the objective lens current width from the previous inspection point based on the laser measurement of the wafer height at the particular position. The processing time Tt from a measurement session to the next measurement session is given as $$Tt = Ts + T1 + \text{Tap}$$

where Tap is the sum of the pattern recognition time and the AF execution time and substantially constant. In the case where the stage speed is controlled in a simple trapezoidal fashion, Ts which is a function of the distance d between the two measurement points is given as, when $d<V\text{max}*V\text{max}/2*(1/\alpha1+1/\alpha2)$, $$Ts=\sqrt{(2d*(1/\alpha1+1/\alpha2))} \text{ and, when } d\geq V\text{max}*V\text{max}/2*1/\alpha1+1/\alpha2)$$

$$Ts=d/V\text{max}+V\text{max}/2*(1/\alpha1+1/\alpha2)$$

where Vmax is the maximum stage speed, $\alpha1$ the acceleration, and $\alpha2$ the deceleration. Also, using the height change $\Delta h$, T1 is expressed as $$T1=A*\exp(\Delta h/\tau)$$

where A and $\tau$ are constants unique to the lens.

These time values are determined for each route so that the total measurement time can be minimized at the time of optimization calculation.

The foregoing description concerns CD-SEM as an example. This invention, however, is not limited to the CD-SEM but applicable also to various electron beam inspection apparatuses with equal effect.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A scanning electron microscope for determining order of irradiation in irradiating an electron beam on one of a plurality of irradiation positions on a sample after focusing is conducted at said one of the plurality of irradiation positions,
   wherein one of a plurality of irradiation orders which a total of focusing time it takes for focusing the electron beam at the irradiation positions in each of said irradiation orders is shorter is selected.

2. The scanning electron microscope according to claim 1, wherein the total of focusing time is determined on the basis of a total of potential variations between the plurality of irradiation positions.

3. The scanning electron microscope according to claim 1, wherein the total of focusing time is determined on the basis of height changes between the plurality of irradiation positions.

4. A scanning electron microscope for determining order of irradiation in irradiating an electron beam on a plurality of irradiation positions on a sample adapted to move in X and Y directions,
   wherein a longer one of respective moving distances of the X and Y directions between the irradiation positions is selected, and the selected ones of moving distances are compared respectively between a plurality of moving routes to select a shorter moving route.

5. A scanning electron microscope comprising a controllable sample stage and a control apparatus for controlling said sample stage so that each of a plurality of positions on said sample automatically moves to an irradiation point of an electron beam in a predetermined order, wherein:
   said sample stage is a XY stage to move said sample in X direction and Y direction, and
   said control apparatus changes said predetermined order based on a condition where a summation of moving times between two of said plurality of positions on said sample is shortened, wherein a longer time of moving times in X direction and Y direction is determined as the moving time between two of said plurality of positions on said sample.

6. The scanning electron microscope according to claim 5, wherein said sample stage moves in X direction independently from in Y direction.

7. A scanning electron microscope comprising a controllable sample stage and a control apparatus for controlling said sample stage so that each of a plurality of positions on said sample automatically moves to an irradiation point of an electron beam in a predetermined order, wherein:
   said control apparatus changes said predetermined order so that a calculated total value of processing times is shortened, wherein said processing time is calculated based on a waiting time of an objective lens to react on a current for the objective lens, which is obtained from a height information of a position on said sample, and based on a summation of moving times between two of said plurality of positions on said sample.

8. The scanning electron microscope according to claim 7, wherein the processing time is a total value of each summation of said moving time between two of said plurality of positions on said sample, said waiting time of said objective lens to react on said current for said objective lens, a pattern recognition time and an auto focus (AF) execution time.

9. A scanning electron microscope comprising a controllable sample stage and a control apparatus for controlling said sample stage so that each of a plurality of positions on said sample automatically moves to the irradiation point of an electron beam in a predetermined order, wherein:
   said control apparatus changes said predetermined order so that a moving route becomes along an equipotential line indicating a distribution of electric potential of said sample.

10. A scanning electron microscope comprising a controllable sample stage and a control apparatus for controlling said sample stage so that each of a plurality of positions on said sample automatically moves to the irradiation point of an electron beam in a predetermined order, wherein:
    said control apparatus changes said predetermined order so that a summation of electric potential differences between two of said plurality of positions on said sample is shortened.

* * * * *